(12) United States Patent
Peabody et al.

(10) Patent No.: US 6,979,299 B2
(45) Date of Patent: Dec. 27, 2005

(54) MEASURING GUIDE FOR USE IN ORTHOPEDIC PROCEDURE

(75) Inventors: Terrance D. Peabody, Flossmoor, IL (US); Richard J. Taft, Austin, TX (US); Richard J. Kana, Austin, TX (US)

(73) Assignee: Zimmer Austin, Inc., Austin, TX (US)

( * ) Notice: Subject to any disclaimer, the term of this patent is extended or adjusted under 35 U.S.C. 154(b) by 372 days.

(21) Appl. No.: 10/068,167

(22) Filed: Feb. 5, 2002

(65) Prior Publication Data

US 2003/0149378 A1 Aug. 7, 2003

(51) Int. Cl.[7] ............................................. A61B 5/103
(52) U.S. Cl. ..................... 600/587; 33/511; 606/102
(58) Field of Search ........................... 600/587, 595, 600/594; 33/511, 512; 606/53, 86, 89, 102

(56) References Cited

U.S. PATENT DOCUMENTS

| | | | | |
|---|---|---|---|---|
| 367,290 A | * | 7/1887 | Gilmer ........................... | 7/164 |
| 762,146 A | * | 6/1904 | Cosbie .......................... | 433/72 |
| 4,220,163 A | * | 9/1980 | Malek Afzali ................ | 600/595 |
| 4,718,850 A | * | 1/1988 | Knebelman ................... | 433/72 |
| 4,893,619 A | * | 1/1990 | Dale et al. ..................... | 606/87 |
| 5,122,145 A | | 6/1992 | Fishbane ....................... | 606/102 |
| 5,156,162 A | * | 10/1992 | Gerhardt ....................... | 600/594 |
| 5,364,401 A | * | 11/1994 | Ferrante et al. ............... | 606/84 |
| 5,486,178 A | | 1/1996 | Hodge ........................... | 606/82 |
| 5,648,891 A | * | 7/1997 | Gierut ........................... | 606/69 |
| 5,662,656 A | * | 9/1997 | White ............................ | 606/88 |
| 5,676,668 A | | 10/1997 | McCue et al. ................. | 606/87 |
| 5,700,268 A | | 12/1997 | Bertin ........................... | 606/102 |
| 5,810,831 A | | 9/1998 | D'Antonio .................... | 606/88 |
| 5,997,545 A | * | 12/1999 | Doherty et al. ............... | 606/102 |
| 6,013,081 A | | 1/2000 | Burkinshaw et al. .......... | 606/88 |
| 6,027,507 A | * | 2/2000 | Anderson et al. ............ | 606/102 |
| 6,077,270 A | | 6/2000 | Katz .............................. | 606/88 |
| 6,105,269 A | * | 8/2000 | Kondrat ........................ | 33/512 |
| 6,193,723 B1 | | 2/2001 | Cripe et al. .................... | 606/88 |
| 6,193,724 B1 | | 2/2001 | Chan ............................. | 606/102 |
| 6,500,179 B1 | * | 12/2002 | Masini .......................... | 606/88 |

FOREIGN PATENT DOCUMENTS

| DE | 3737993 A | * | 5/1989 | ............ A61B 5/10 |
|---|---|---|---|---|
| FR | 2659224 A1 | * | 9/1991 | ............ A61B 17/56 |

* cited by examiner

Primary Examiner—Charles Marmor
(74) Attorney, Agent, or Firm—Jonathan D. Feuchtwang; Zimmer Technology, Inc.

(57) ABSTRACT

A measuring guide for use in various surgical procedures. The measuring guide is a noninvasive tool that may be repeatedly applied to a desired bone member to make appropriate measurements. The measuring guide allows for easy adjustment of the distance between a stop plate designed to engage an end of a given bone member and a marking guide used to facilitate marking of the bone. Additionally, the stop plate may be pivotably mounted to facilitate ease and accuracy of measurement.

21 Claims, 11 Drawing Sheets

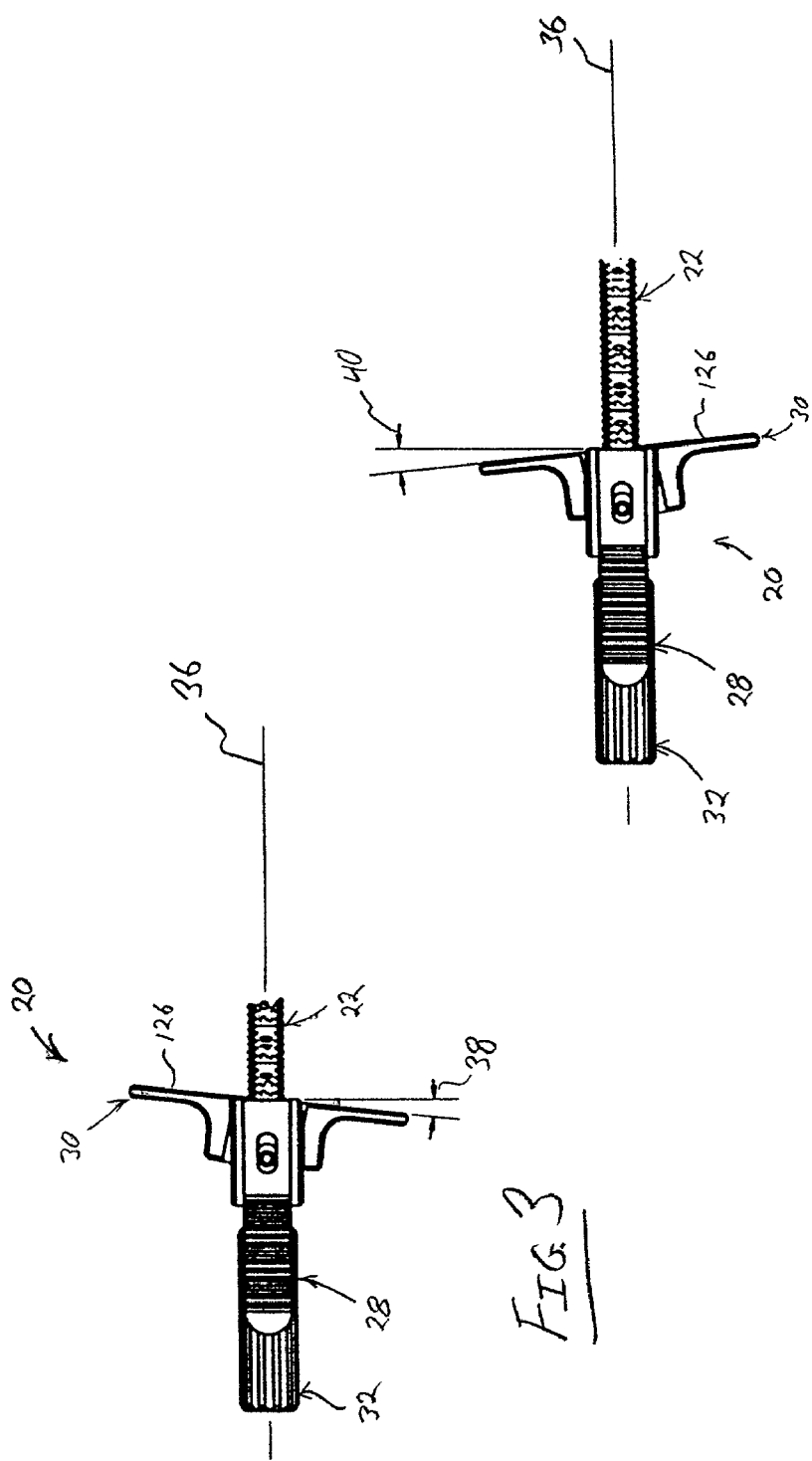

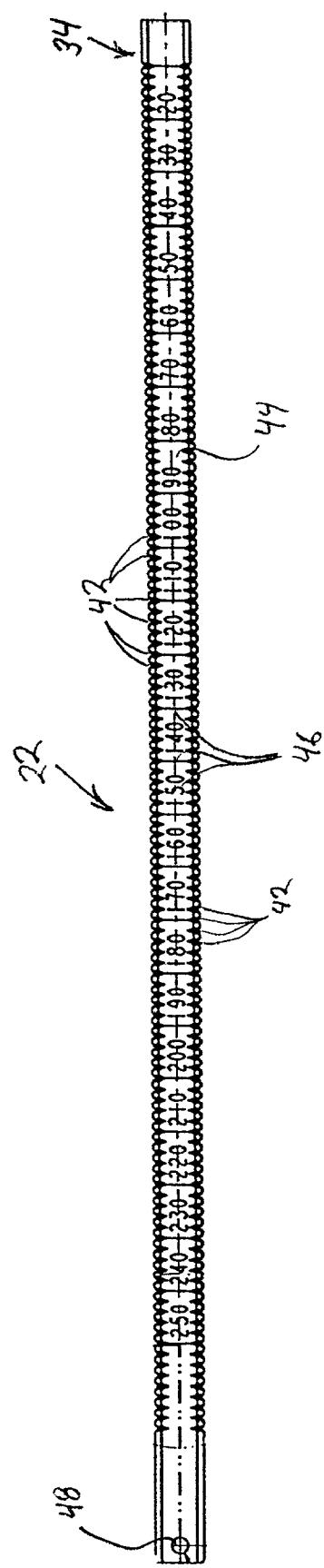

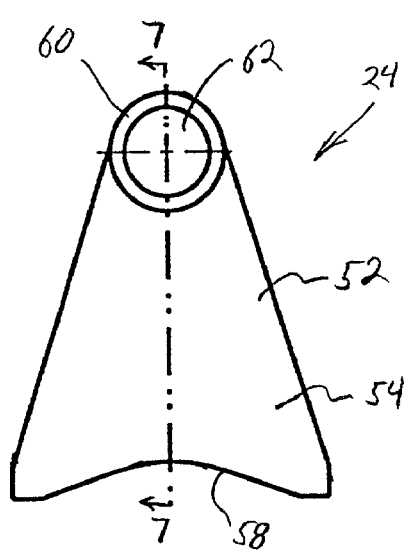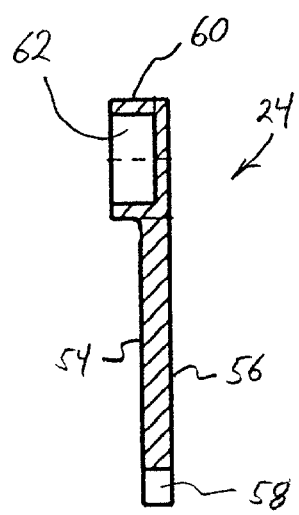
FIG. 6
FIG. 7

MEASURING GUIDE FOR USE IN ORTHOPEDIC PROCEDURE

FIELD OF THE INVENTION

The present invention relates generally to instruments for use in orthopedic procedures, and particularly to a noninvasive measuring device to facilitate certain of those procedures.

BACKGROUND OF THE INVENTION

In a variety of orthopedic procedures, such as oncological procedures, primaries and revisions, measurements are made to obtain a desired result. In some primary and oncological procedures, for example, a section of the bone is removed and an orthopedic prosthesis is attached. Once bone tissue is removed, it becomes difficult to locate the prosthesis at a desired position. Consequently, measurements often are made and reference points are marked for removal of bone tissue. The reference markings may then be used to facilitate location of the prosthesis.

Similarly, in revision procedures, an orthopedic implant is replaced due to, for example, aseptic loosening infection, wear, etc. In such procedures, the surgeon uses reference marks or bone landmarks that allow the surgeon to initially set joint lines for the revisions. Such reference points help reestablish the desired joint line for the replacement orthopedic implant after the old orthopedic implant and a certain amount of bone tissue is removed.

Some instruments have been constructed to facilitate such procedures by aiding in the location of the prosthesis being implanted. However, typical instruments require an invasive procedure, such as attachment of the device to bone tissue by screws or other types of fasteners. Additionally, such instruments often do not account for the natural shape of specific bones, such as the femur or tibia. The present invention addresses these and other drawbacks of existing techniques and instruments.

SUMMARY OF THE INVENTION

The following passage is intended only to provide a brief summary of limited aspects of the present invention and should not be construed as encompassing all necessary elements or steps of the inventions.

The present invention relates generally to a technique for locating a prosthetic device during an orthopedic procedure. The technique utilizes a noninvasive measuring guide able to assist in locating the prosthetic device at, for example, a desired joint line. Generally, the measuring guide comprises a noninvasive marking guide to facilitate marking of a reference point on a desired region of bone tissue. The guide further comprises a noninvasive stop plate designed to abut an end of the bone undergoing the procedure. Examples include the distal femoral condyles of the femur or the proximal end of a tibia.

The marking guide and the stop plate are adjustably connected to one another to facilitate accurate marking along the marking guide at a desired distance from the stop plate. Once the reference marks are made, the measuring guide may subsequently be used to locate the prosthetic device at a desired location, e.g. to establish a predetermined joint line.

BRIEF DESCRIPTION OF THE DRAWINGS

The invention will hereafter be described with reference to the accompanying drawings, wherein like reference numerals denote like elements, and:

FIG. 3 is a top view of a portion of the measuring guide illustrated in FIG. 1;

FIG. 4 is a top view similar to that of FIG. 3;

FIG. 5 is a top view of a ruler member utilized in the exemplary measuring guide;

FIG. 6 is an end view of an exemplary marking guide;

FIG. 7 is a cross-sectional view taken generally along line 7—7 of FIG. 6;

DETAILED DESCRIPTION OF EXEMPLARY EMBODIMENTS

It will be appreciated that the present invention can take many forms and embodiments. Some embodiments of the invention are described so as to give an understanding of the invention. It is not intended, however, that the embodiments of the present invention that are described in this specification should limit the invention.

Figure 1:
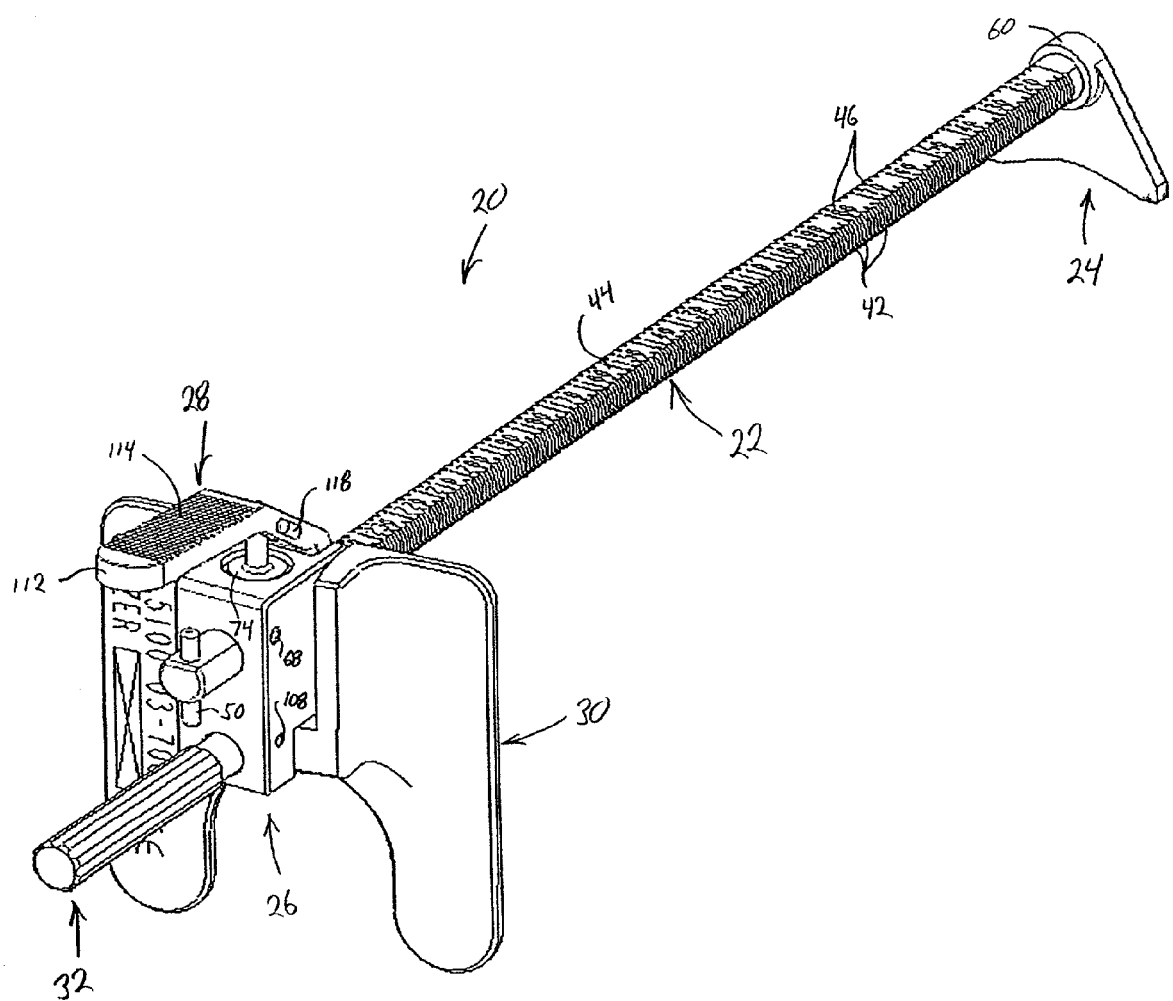
FIG. 1 is a perspective view of an exemplary measuring guide according to one embodiment of the present invention.

Referring generally to FIG. 1, a measuring guide 20 is illustrated according to one embodiment of the present invention. Measuring guide 20 generally comprises a ruler member 22 coupled to a marking guide 24. The measuring guide 20 further comprises a locking mechanism 26, a lever 28, a stop plate 30 and a handle 32.

As will be explained in greater detail below, stop plate 30 is designed to abuttingly engage the end of a bone member being measured, such as the distal femoral condyles of a femur or the proximal end of a tibia. Similarly, marking guide 24 is a noninvasive member designed to rest on or proximate the side of a bone being measured. The distance between stop plate 30 and marking guide 24 is readily adjustable to permit marking of bone tissue a desired distance from the end of the bone member abutting stop plate 30. By maintaining this desired distance, measuring guide 20 may readily be used again during attachment of a prosthetic device to locate the prosthetic device at, for example, a desired joint line. Alternatively, the distance between stop plate 30 and marking guide 24 may be lengthened or shortened to help accurately change the final joint line from that of the original.

Figure 2:
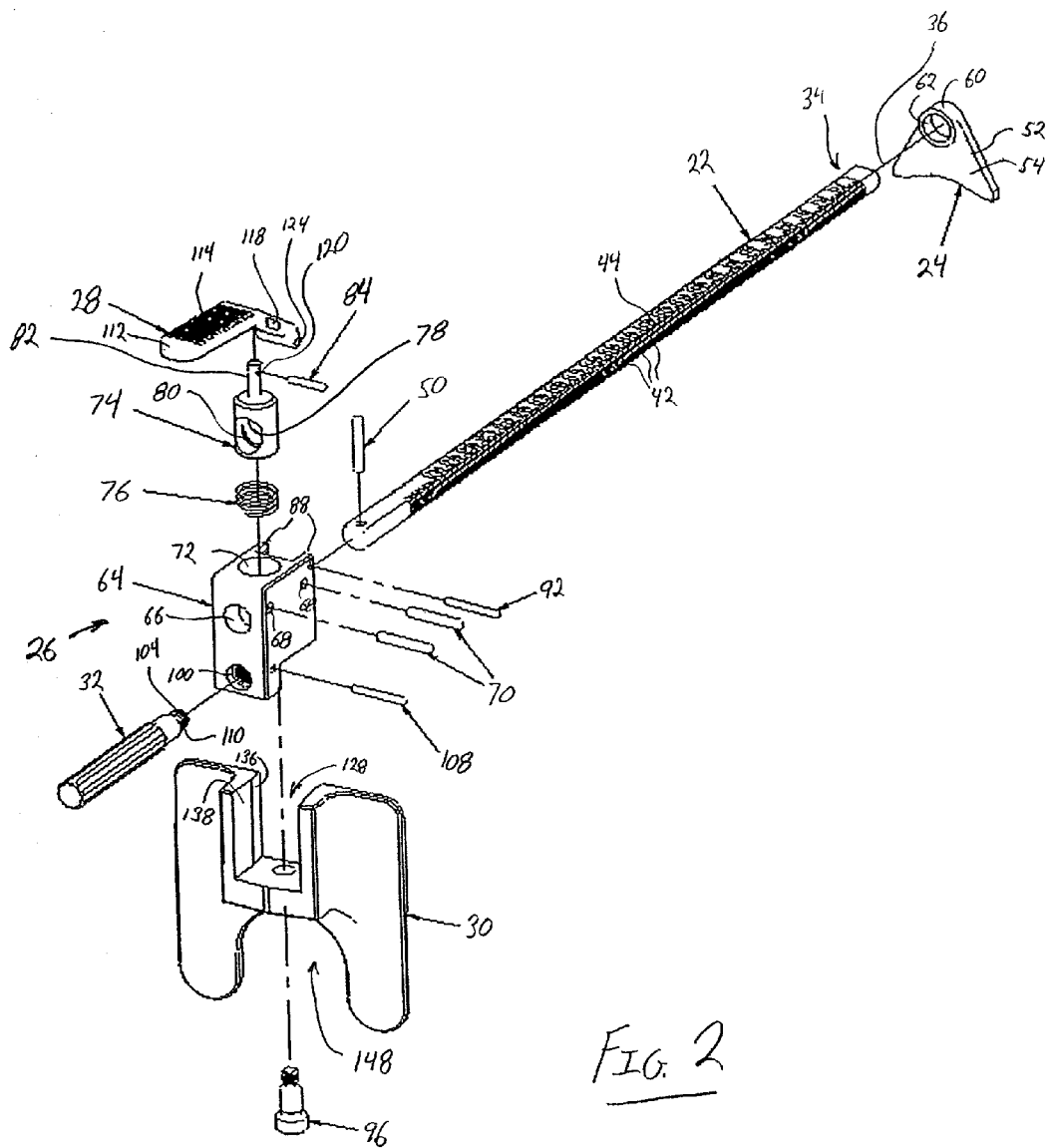
FIG. 2 is an exploded view of the measuring guide illustrated in FIG. 1.

With reference to FIG. 2 and subsequent figures, the details of various components as well as the interaction of those components is explained. In this embodiment, marking guide 24 is affixed to ruler member 22 at a marking end 34 of the ruler. Generally opposite marking guide 24, ruler 22 is slidingly received by locking mechanism 26, and stop plate 30 is mounted to locking mechanism 26. Thus, the distance between marking guide 24 and stop plate 30 may be adjusted by sliding locking mechanism 26 along ruler 22.

In the embodiment illustrated, stop plate 30 is pivotably mounted to locking mechanism 26 such that it may be pivoted through selected angles with respect to a longitudinal axis 36 of ruler 22, as further illustrated in FIGS. 3 and 4. The range of angles through which stop plate 30 is designed to pivot may be adjusted according to the type of bone member being measured and/or according to specific aspects of a given procedure.

For example, it has been determined that a plane adjacent the distal femoral condyles of an average femur is not perpendicular to the longitudinal axis of the femur but rather lies approximately six degrees from perpendicular. Accordingly, an exemplary measuring guide may be designed to permit pivoting of stop plate 30 to positions generally perpendicular to longitudinal axis 36, approximately minus six degrees from perpendicular, as indicated by angle 38 in FIG. 3, and approximately plus six degrees from perpendicular, as indicated by angle 40 illustrated in FIG. 4. In other words, stop plate 30 may be pivoted to angles of approximately 84 degrees, 90 degrees and 96 degrees with respect to longitudinal axis 36. This facilitates a more natural, unstrained placement of marking guide 24 at a desired location while stop plate 30 rests in abutting engagement with the distal femoral condyles of the femur. However, measuring guide 20 may be designed such that stop plate 30 is pivotable to angles other than those discussed above. Additionally, stop plate 30 may be permitted to pivot between multiple angular positions or limited to selected positions, such as the 84, 90 and 96 degree positions.

Although the specific design and size of various components of measuring guide 20 may vary without departing from the scope of the present invention, specific, exemplary components are described to facilitate understanding of the use and interaction of the various components. For example, an exemplary ruler 22 is illustrated in FIGS. 2 and 5 and comprises a plurality of grooves 42. Additionally, the exemplary ruler 22 comprises at least one flat side 44 providing a generally D-shaped cross-section. A plurality of measurement marks 46 are placed along flat side 44 to permit easy determination of the distance between marking guide 24 and stop plate 30. In the embodiment illustrated, measurement marks 46 indicate a distance from 10 millimeters to 250 millimeters with grooves 42 spaced at 2 millimeter intervals. However, this range and the distance between grooves can be adjusted depending on various design parameters.

Opposite from marking end 34, ruler 22 comprises a retention feature 48 to prevent inadvertent removal of ruler 22 from locking mechanism 26. For example, retention feature 48 may comprise a hole sized to receive a press fit pin 50 (See FIG. 2).

With reference to FIGS. 2, 6 and 7, an exemplary marking guide 24 is illustrated. In this embodiment, marking guide 24 comprises a plate region 52 having an inner surface 54 and an outer surface 56. Outer surface 56 is generally flat and used to guide the marking of bone tissue. The marking may be accomplished by moving an appropriate surgical marking pen, scalpel or osteotome along outer surface 56 against the adjacent bone tissue. Plate region 52 further comprises an abutment surface 58 designed to rest against the bone member during either marking or subsequent measuring based on the applied reference marks. Abutment surface 58 is generally concave to better enable placement and retention against the curvature of a typical bone.

Figure 8:
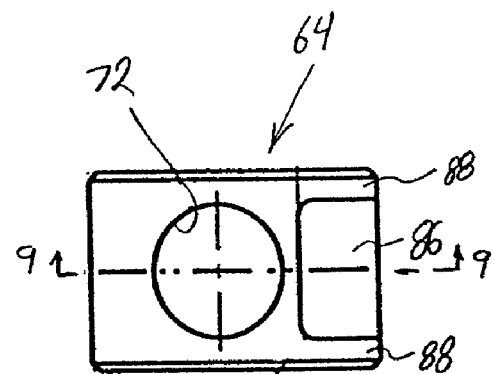
FIG. 8 is a top view of a support block utilized in the measuring guide illustrated in FIG. 1.
Figure 9:
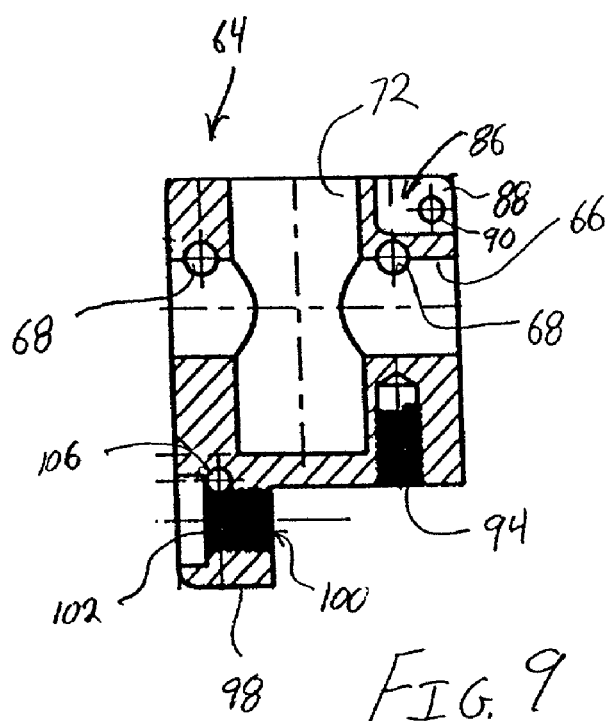
FIG. 9 is a cross-sectional view taken generally line 9—9 of FIG. 8.

Marking guide 24 further comprises a boss 60 generally opposite abutment surface 58. Boss 60 includes a recessed region 62 sized to receive marking end 34 of ruler 22. Boss 60 may be secured to ruler 22 by, for example, appropriate weldments, adhesives, set screws or other fasteners. Referring again to FIG. 2 along with FIGS. 8 and 9, an exemplary locking mechanism 26 comprises a block 64 having a longitudinal opening 66 therethrough. Longitudinal opening 66 is sized to slidably receive ruler 22. Block 64 is retained on ruler 22 by marking guide 24 and retention pin 50, respectively.

Additionally, block 64 comprises a pair of generally transverse pin openings 68 sized to receive corresponding pins 70 (see FIG. 2). Pins 70 are positioned to lie along flat side 44 of ruler 22 to prevent rotation of ruler 22 within block 64. In an exemplary procedure, pins 70 are pressed into pin openings 68, welded and machine flush finished.

Block 64 also includes a release mechanism receptacle 72. Release mechanism receptacle 72 intersects longitudinal opening 66 and is sized to receive a slidable release mechanism 74. In the illustrated embodiment, release mechanism 74 is biased in a direction out of release mechanism receptacle 72 by a spring member 76, such as a coil spring. The spring member 76 is disposed in release mechanism receptacle 72 beneath release mechanism 74.

With further reference to FIG. 2, release mechanism 74 may be generally cylindrical having a transverse opening 78. Transverse opening 78 is sized to slidably receive ruler 22 therethrough. In the particular embodiment illustrated, release mechanism 74 includes one or more ridges 80 extending radially inwardly within transverse opening 78. The one or more ridges 80 are sized to engage grooves 42 of ruler 22.

Thus, release mechanism 74 may be pressed against the spring bias of spring member 76 while ruler 22 is moved through longitudinal opening 66 of block 64 and transverse opening 78 of release mechanism 74. Once this force is removed, spring member 76 biases the one or more ridges 80 into engagement with corresponding grooves 42 to securely hold the block 64 and ruler 22 at a fixed location with respect to one another. Release mechanism 74 further comprises an extension 82 that extends outwardly from release mechanism receptacle 72 for engagement with lever 28 via a lever retention pin 84.

Furthermore, block 64 comprises a recessed portion 86 for pivotably receiving lever 28. Recessed portion 86 is partially defined by a pair of end walls 88 having corresponding openings 90 therethrough. Openings 90 are sized to receive a pivot pin 92 (see FIG. 2) to pivotably secure an end of lever 28 in recessed portion 86.

Block 64 comprises a threaded opening 94 by which stop plate 30 is pivotably secured to block 64 via a threaded fastener 96, such as a shoulder screw. Block 64 also includes a handle attachment region 98 having a handle retention opening 100 for receiving handle 32. In the embodiment illustrated, the axis of handle retention opening 100 is generally perpendicular to the axis of threaded opening 94. This permits handle 32 to be used as a stabilization member to lock stop plate 30 at a desired angle.

For example, handle retention opening 100 may have a threaded region 102 to threadably receive a corresponding threaded region 104 of handle 32. When handle 32 is threaded outwardly, stop plate 30 is freely pivotable. However, once stop plate 30 is at a desired position, handle 32 is threaded inwardly into engagement with the stop plate 30 to secure the stop plate at a desired angle.

Additionally, block 64 may comprise a retention pin opening 106 extending through handle attachment region 98 generally transverse to handle retention opening 100. Opening 106 is sized to receive a handle retention pin 108 (see FIG. 2). Furthermore, handle 32 comprises an annular recessed region 110 between threaded region 104 and the remainder of handle 32. Handle retention pin 108 is positioned to interfere with threaded region 104 when handle 32 is backed out of block 64 a distance sufficient to permit pivoting of stop plate 30. This prevents handle 32 from inadvertent separation with block 64.

Figure 10:
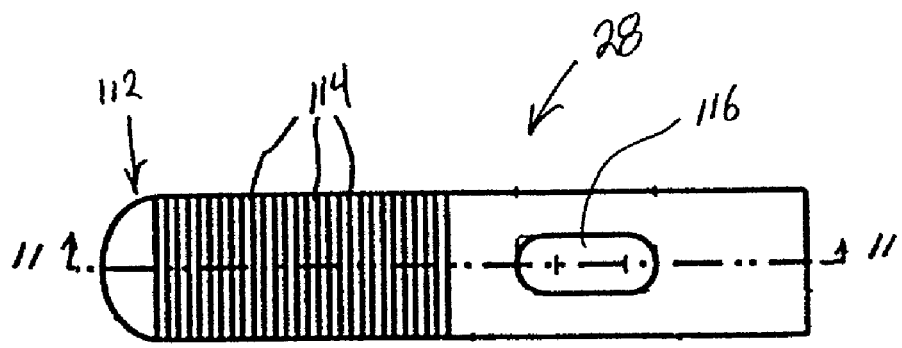
FIG. 10 is a top view of a lever utilized in the measuring guide illustrated in FIG. 1.
Figure 11:
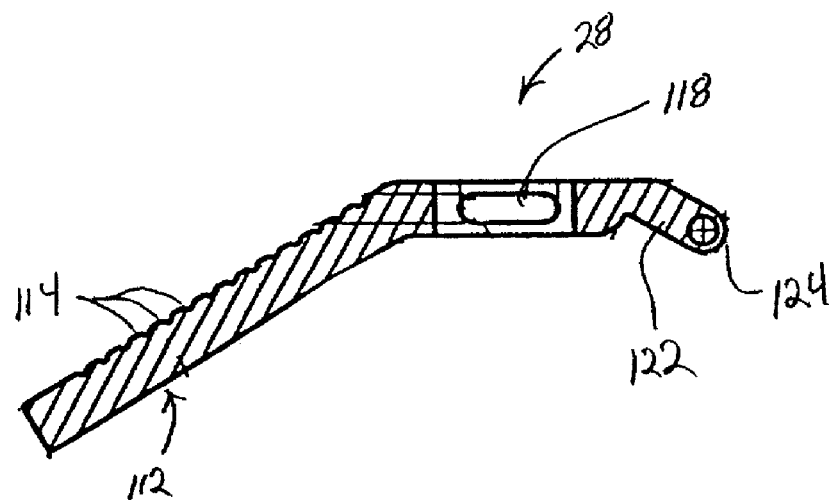
FIG. 11 is a cross-sectional view taken generally along line 11—11 of FIG. 10.

With further reference to FIG. 2 and also FIGS. 10 and 11, an exemplary lever 28 is illustrated. Lever 28 comprises a gripping portion 112 that may have a plurality of ridges 114 or other gripping mechanisms. Ridges 114 facilitate actuation or movement of gripping portion 112 by an individual adjusting the distance between stop plate 30 and marking guide 24. As illustrated best in FIG. 10, lever 28 also comprises an elongate opening 116 for receiving extension 82 of release mechanism 74. Extension 82 is held in elongate opening 116 by lever retention pin 84. Pin 84 extends through a generally transverse elongate opening 118 and an aligned opening 120 disposed transversely through extension 82, as best illustrated in FIG. 2. By way of example, elongate opening 116 and transverse elongate opening 118 may be sized to permit sliding motion of extension 82 and lever retention pin 84, respectively. Opening 120 of extension 82, on the other hand, may be sized for a press fit with lever retention pin 84 to hold the pin at a desired position with respect to transverse elongate opening 118.

Additionally, lever 28 comprises a pivot portion 122 having a transverse pivot opening 124 therethrough. Pivot opening 124 is sized to receive pivot pin 92. Thus, when lever 28 is engaged with block 64 via pivot pin 92, gripping portion 112 is simply pressed to move release mechanism 74 against spring member 76 for adjustment of the distance between stop plate 30 and marking guide 24.

Figure 12:
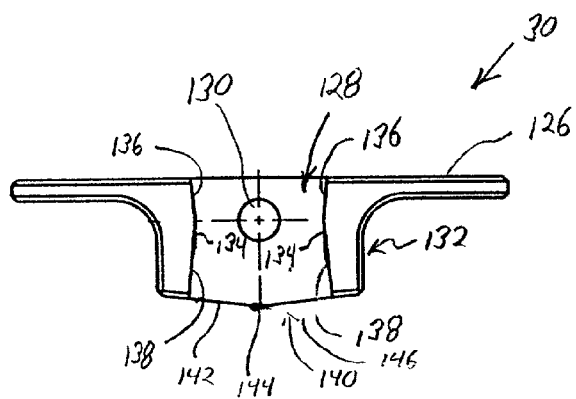
FIG. 12 is a top view of an exemplary stop plate used in the measuring guide illustrated in FIG. 1.
Figure 13:
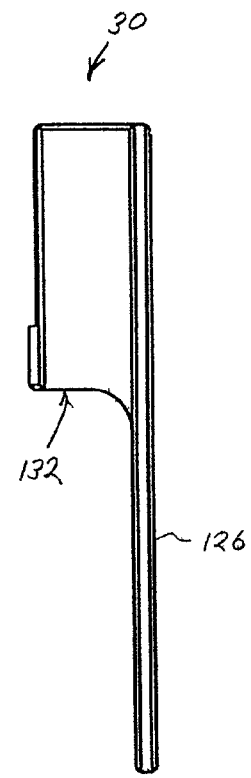
FIG. 13 is a side view of the stop plate illustrated in FIG. 12.

Referring again to FIG. 2 along with FIGS. 12 and 13, an exemplary stop plate 30 comprises an abutment surface 126 positioned to abuttingly engage the end of a bone member. Stop plate 30 further comprises a cutout region 128 sized to receive block 64. A fastener opening 130 extends to cutout region 128 and is sized to receive threaded fastener 96 when threaded fastener 96 is inserted through opening 130 and threadably engaged with block 64 via threaded opening 94. Fastener opening 130 allows stop plate 30 to pivot about threaded fastener 96.

Additionally, cutout region 128 extends from abutment surface 126 through an expanded portion 132 and is defined by a pair of side walls 134. Exemplary side walls 134 each comprise a pair of angled wall sections 136 and 138, respectively, that permit pivotal motion of stop plate 30 through the desired angular range.

Additionally, expanded portion 132 may comprise an outer face 140 having a plurality of angled wall sections, e.g. wall sections 142, 144 and 146, respectively. Angled wall sections 142, 144 and 146 correspond to desired angular positions of stop plate 30 and are generally aligned with handle 32. For example, wall sections 142, 144 and 146 may correspond to the perpendicular, plus six degree and minus six degree positions relative to ruler 22, as discussed above. When handle 32 is tightened against a desired angled wall section, the stop plate 30 is locked at that specific angular position for use in making measurements on a desired bone member. Furthermore, stop plate 30 may have an opened area 148 (see FIG. 2) to promote greater visibility of the end of the bone member when aligning measuring guide 20.

Figure 14:
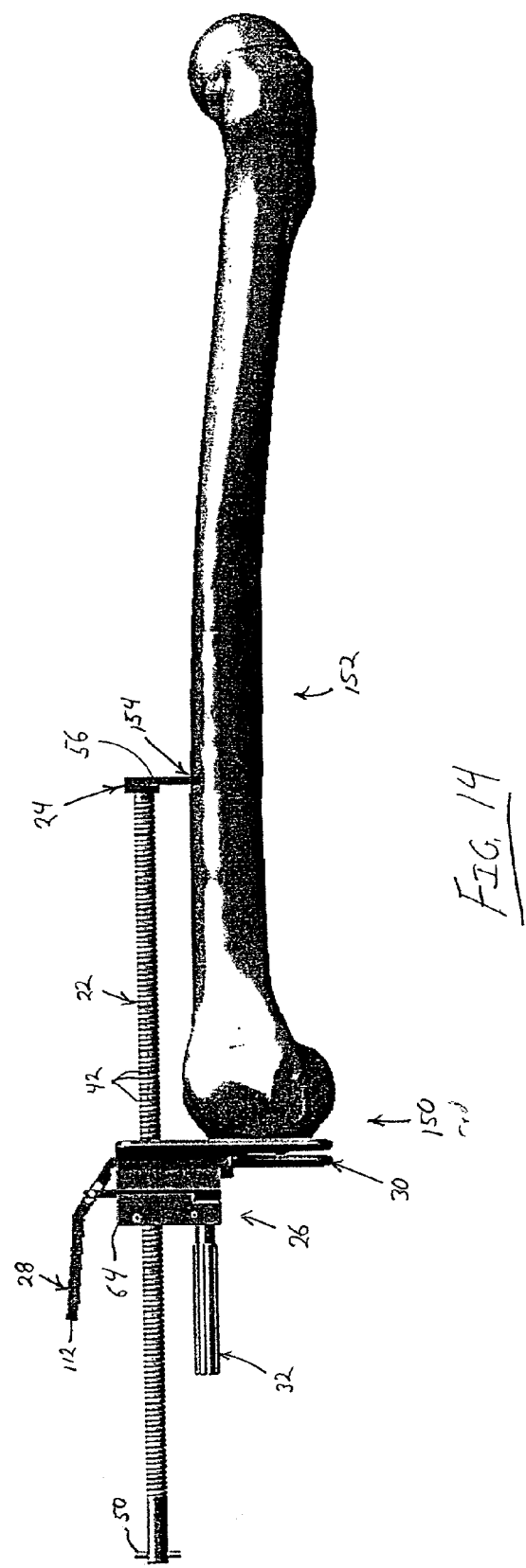
FIG. 14 is a side view of the measuring guide positioned against a representative femur.

In operation, the desired angle of stop plate 30 and the desired distance between stop plate 30 and marking guide 24 are initially set, and measuring guide 20 is deployed against a bone member in a noninvasive manner. For example, stop plate 30 may be brought into abutment with an end 150 of a bone member 152, such as the exemplary femur illustrated in FIG. 14. In this example, stop plate 30 is pivoted to the desired six degree angle and moved into contact with the distal femoral condyles of end 150. The distance between stop plate 30 and marking guide 24 is preselected based on, for example, the amount of bone material to be removed in an oncological procedure. The bone tissue is then marked along outer surface 56 of marking guide 24 as indicated by arrow 154. Thus, a desired joint line has been established a predetermined distance from the marked area 154.

Measuring guide 20 is removed during the oncological procedure in which diseased bone tissue is removed. Upon removal of the tissue, marking guide 24 is again aligned with marked area 154 such that stop plate 30 may be used as a guide in determining proper positioning of a prosthetic device. For example, the practitioner is able to readily select the appropriately sized spacer or spacers to place between the resected bone and the new implant to ensure the implant establishes a joint line at either the old location or at a desired incremental distance from the joint line of the original bone.

Figure 15:
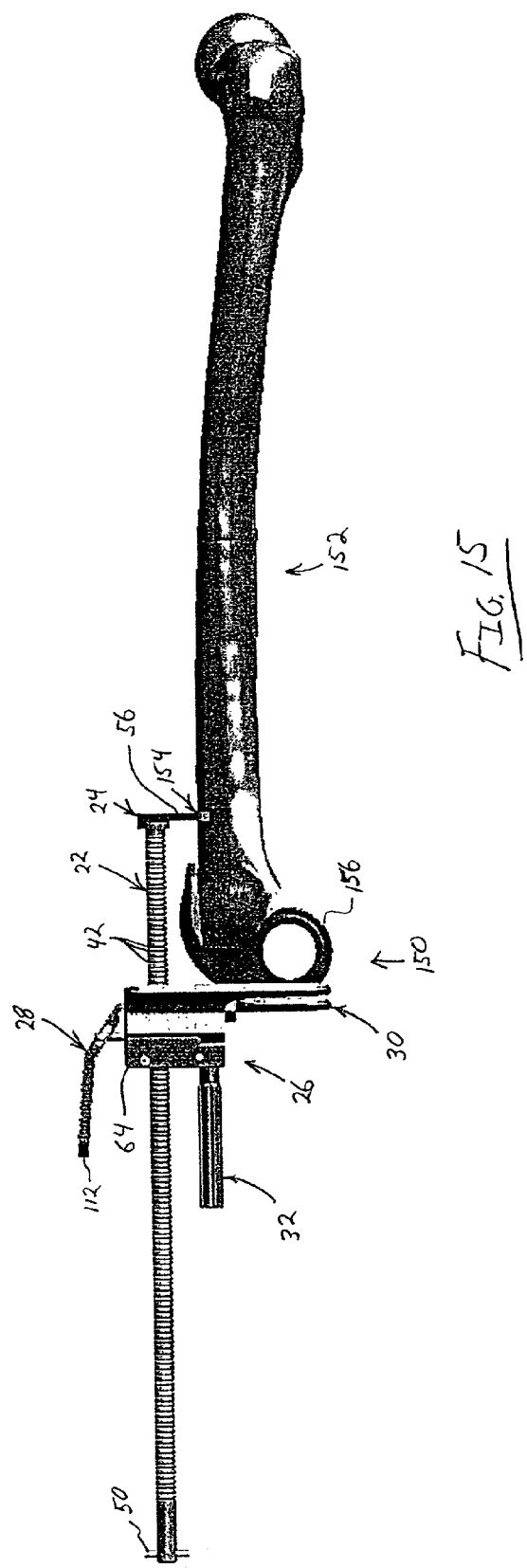
FIG. 15 is a side view of the measuring guide positioned against an exemplary prosthetic device attached to a representative femur.

Another example of a procedure in which measuring guide 20 is utilized is a revision. In such a procedure, a desired angle of stop plate 30 and the distance between stop plate 30 and marking guide 24 is preselected. The stop plate is then positioned in abutting engagement with end 150 of bone member 152, as illustrated in FIG. 15. In this procedure, bone member end 150 comprises an orthopedic device 156 selected for replacement.

Measuring guide 20 is used to measure a selected distance from the distal surface of the old orthopedic device 156 to a point on the bone which is then marked as indicated by arrow 154. Subsequently, measuring guide 20 is lifted away and the old orthopedic device 156 is removed. The practitioner then resects the bone to establish a good surface for receiving a new orthopedic implant. By placing marking guide 24 back at the marked area 154, the practitioner is once again able to select the appropriately sized spacer or spacers to place between the resected bone and the new implant to establish a desired joint line at the previous location or at an adjusted location. In either of the procedures discussed above, if the new joint line is different from the original joint line, the distance between stop plate 30 and marking guide 24 is simply adjusted incrementally, as described above.

Figure 16:
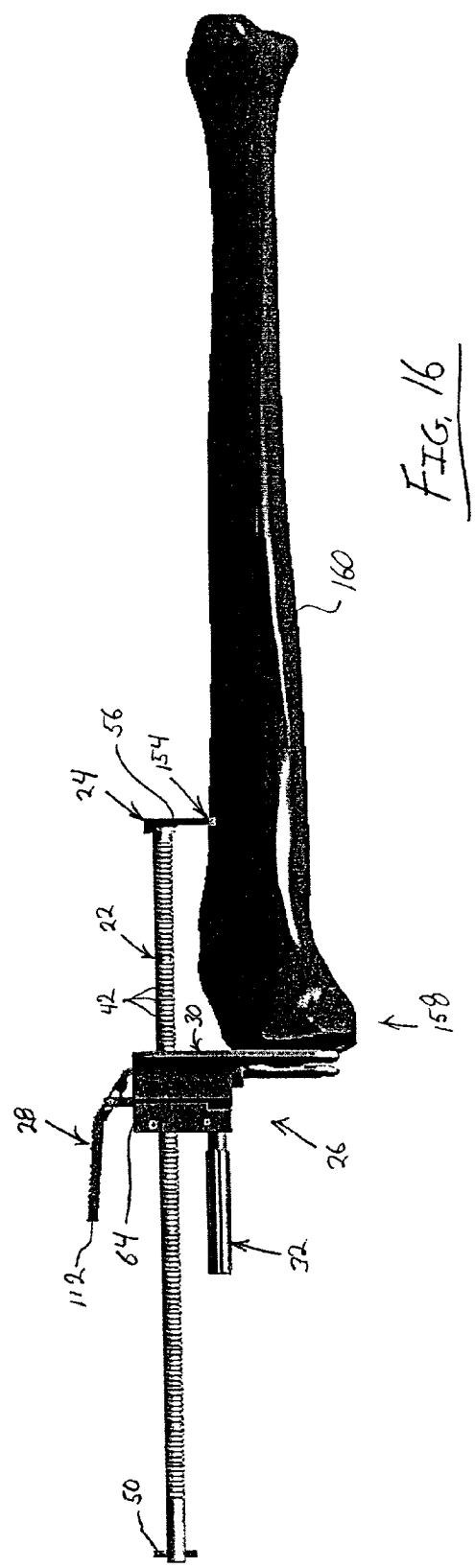
FIG. 16 is a side view of the measuring guide positioned against the proximal end of a tibia.

Although the exemplary procedures described above have been performed on a femur, measuring guide 20 also can be used on other bone members, such as the tibia illustrated in FIG. 16. In this example, stop plate 30 is moved into abutting engagement with a proximal end 158 of a tibia 160. The measuring guide 20 is used to facilitate desired procedures on the tibial bone member, as described above with respect to the femur.

It will be understood that the foregoing description is of exemplary embodiments of this invention, and that the invention is not limited to the specific form shown. For example, the various size and configuration of individual components of the measuring guide may be changed according to desired procedure parameters or size and type of the bone member to which the measuring guide is applied; the materials from which the measuring guide is made may vary but typically are selected from materials appropriate for surgical procedures, such as surgical stainless steel; and the measuring guide also may be used to provide a variety of other types and numbers of measurements for other procedures. These and other modifications may be made in the design and arrangement of the elements without departing from the scope of the invention as expressed in the dependent claims.

What is claimed is:

1. A measuring guide for assisting in locating a prosthetic device during an orthopedic procedure, comprising:
    a marking guide adapted to facilitate marking of a bone tissue at a desired location;
    a stop plate;
    a ruler, including a top, a bottom and two sides, the ruler being coupled to the marking guide and to the stop plate, and the ruler indicating the distance between the marking guide and the stop plate, wherein the stop plate includes an abutment surface, configured to abut a bone, and further wherein the abutment surface is positioned on both sides of the ruler; and
    a locking mechanism that cooperates with the ruler to permit selective adjustment of the distance between the marking guide and the stop plate by moving the stop plate with respect to the ruler, wherein the marking guide and the stop plate are utilized in a manner noninvasive to the bone tissue, and further wherein the stop plate is pivotably coupled to the locking mechanism to permit positioning of the stop plate at desired angles with respect to the ruler.

2. The measuring guide as recited in claim 1, wherein the abutment surface of the stop plate is configured to abut the distal femoral condyles.

3. The measuring guide as recited in claim 1, wherein the abutment surface of the stop plate is configured to abut the proximal end of a tibia.

4. The measuring guide as recited in claim 1, wherein the stop plate is adapted to be locked at desired angles with respect to the ruler.

5. The measuring guide as recited in claim 4, wherein the desired angles are approximately 84°, 90°, and 96°.

6. The measuring guide as recited in claim 1, wherein the locking mechanism comprises an opening through which the ruler is received and a release mechanism to selectively release the ruler for sliding movement through the opening.

7. The measuring guide as recited in claim 6, wherein the ruler comprises a flat side and a series of periodic grooves, and the release mechanism comprises at least one corresponding protrusion to engage selected grooves of the series of periodic grooves.

8. The measuring guide as recited in claim 7, further comprising a handle coupled to the locking mechanism and a lever coupled to the release mechanism to permit selective engagement and disengagement of the release mechanism and the ruler.

9. The measuring guide as recited in claim 1, wherein said locking mechanism includes an opening, and said ruler is configured to slide within said opening.

10. The measuring guide as recited in claim 1, wherein said ruler is a rigid member that extends the full length between the marking guide and the stop plate and said ruler includes a series of markings to indicate the distance between the marking guide and the stop plate, and further wherein when the stop plate is moved along the ruler towards the marking guide, the distance between the stop plate and the marking guide decreases.

11. The measuring guide as recited in claim 1, wherein said ruler is a rigid member that extends the full length between the marking guide and the stop plate.

12. A measuring guide for noninvasive measurement of bone tissue during an orthopedic procedure, comprising:
    a noninvasive marking guide;
    a ruler coupled to the marking guide;
    a noninvasive stop plate coupled to the ruler, the noninvasive stop plate being pivotable, with respect to a pivot point on the ruler, to facilitate transverse placement, with respect to the ruler, against an end surface of a bone; and
    a locking mechanism that permits selective adjustment of the distance between the noninvasive marking guide and the noninvasive stop plate,
    wherein the ruler indicates the distance between the noninvasive marking guide and the noninvasive stop plate,
    wherein the locking mechanism comprises:
        a block having an opening slidingly receiving the ruler; and
        a spring-loaded release mechanism biased toward engagement with the ruler to lock the ruler at a desired location with respect to the block.

13. The measuring guide as recited in claim 12, wherein the noninvasive stop plate is pivotably mounted to the block.

14. The measuring guide as recited in claim 13, further comprising a handle coupled to the block, wherein the handle is adjustable to selectively lock the noninvasive stop plate at a desired angle with respect to the ruler.

15. The measuring guide as recited in claim 12, further comprising a lever coupled to the release mechanism to permit selective disengagement of the release mechanism from the ruler.

16. A measuring guide for noninvasive measurement of bone tissue during an orthopedic procedure, comprising:
    a noninvasive marking guide;
    a ruler coupled to the marking guide, the ruler defining a longitudinal axis and a transverse axis;
    a noninvasive stop plate coupled to the ruler, the noninvasive stop plate being pivotable, with respect to the transverse axis of the ruler, to facilitate transverse placement, with respect to the ruler, of an abutment surface of the stop plate against an end surface of a bone, wherein the abutment surface is generally symmetric with respect to both sides of the longitudinal axis defined by the ruler; and
    a locking mechanism that permits selective adjustment of the distance between the noninvasive marking guide and the noninvasive stop plate,
    wherein the ruler indicates the distance between the noninvasive marking guide and the noninvasive stop plate.

17. The measuring guide as recited in claim 16, wherein the stop plate is configured to abut the distal femoral condyles.

18. The measuring guide as recited in claim 16, wherein the stop plate is configured to abut the proximal end of the tibia.

19. The measuring guide as recited in claim 16, wherein said locking mechanism includes an opening, and said ruler is configured to slide within said opening.

20. The measuring guide as recited in claim 16, wherein said ruler is a rigid member that extends the full length between the marking guide and the stop plate.

21. A measuring guide for noninvasive measurement of bone tissue during an orthopedic procedure, comprising:
- a noninvasive marking guide;
- a ruler coupled to the marking guide, the ruler defining a longitudinal axis;
- a noninvasive stop plate coupled to the ruler, the noninvasive stop plate being pivotable, with respect to a pivot point on the ruler, to facilitate transverse placement, with respect to the ruler, of an abutment surface of the stop plate against an end surface of a bone, wherein the abutment surface is generally symmetric with respect to both sides of the longitudinal axis defined by the ruler; and
- a locking mechanism that permits selective adjustment of the distance between the noninvasive marking guide and the noninvasive stop plate,
- wherein the ruler indicates the distance between the noninvasive marking guide and the noninvasive stop plate;
- wherein the noninvasive stop plate is selectively lockable at angles of approximately 84°, 90° and 96° relative to the ruler.

* * * * *